US00PP16061P2

(12) United States Plant Patent
Dekker

(10) Patent No.: US PP16,061 P2
(45) Date of Patent: Oct. 25, 2005

(54) ***CHRYSANTHEMUM* PLANT NAMED 'DEKLACETTI'**

(50) Latin Name: *Chrysanthemum×morifolium*
Varietal Denomination: DekLacetti

(75) Inventor: Nicolaas P. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 84 days.

(21) Appl. No.: 10/888,829

(22) Filed: Jul. 9, 2004

(51) Int. Cl.[7] ..... A01H 5/00
(52) U.S. Cl. ..... Plt./296
(58) Field of Search ..... Plt./296

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'DekLacetti', characterized by its daisy-type inflorescences with orange-colored ray florets and green-colored disc florets; strong and upright flowering stems; freely flowering habit; uniform flowering response; and good postproduction longevity.

1 Drawing Sheet

Botanical classification/cultivar designation: *Chrysanthemum×morifolium* cultivar DekLacetti.

BACKGROUND OF THE INVENTION

The present invention relates to a new and distinct cultivar of *Chrysanthemum* plant, botanically known as *Chrysanthemum×morifolium* and referred to by the name 'DekLacetti'.

The new *Chrysanthemum* is the product of a planned breeding program conducted by the Inventor in Hensbroek, The Netherlands. The objective of the breeding program is to create new cut *Chrysanthemum* cultivars with interesting inflorescence forms and attractive floret coloration.

The new *Chrysanthemum* originated from a cross-pollination made by the Inventor on Sep. 25, 2001, in Hensbroek, The Netherlands, of a proprietary selection of *Chrysanthemum* identified as code number 5003,75, not patented, as the female, or seed, parent with a proprietary *Chrysanthemum* selection identified as code number 99.619, 01, not patented, as the male, or pollen, parent. The new *Chrysanthemum* was discovered and selected by the Inventor as a single plant within the progeny of the stated cross-pollination in a controlled environment in Hensbroek, The Netherlands.

Asexual reproduction of the new *Chrysanthemum* by terminal cuttings in Hensbroek, The Netherlands since April, 2002, has shown that the unique features of this new *Chrysanthemum* are stable and reproduced true to type in successive generations.

BRIEF SUMMARY OF THE INVENTION

The cultivar DekLacetti has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'DekLacetti'. These characteristics in combination distinguish 'DekLacetti' as a new and distinct cultivar:

1. Daisy-type inflorescences with orange-colored ray florets and green-colored disc florets; typically grown as a spray type.
2. Strong and upright flowering stems.
3. Freely flowering habit.
4. Uniform flowering response.
5. Good postproduction longevity.

Compared to plants of the female parent selection, plants of the new *Chrysanthemum* have thicker stems, smaller leaves and differ in ray floret coloration as plants of the female parent have pink-colored ray florets.

Compared to plants of the male parent selection, plants of the new *Chrysanthemum* have larger inflorescences and differ in ray floret coloration as plants of the male parent have white-colored ray florets.

Plants of the new *Chrysanthemum* can be compared to plants of the *Chrysanthemum* cultivar Managua Orange, disclosed in U.S. Plant Pat. No. 15,130. In side-by-side comparisons conducted in Hensbroek, The Netherlands, plants of the new *Chrysanthemum* differed primarily from plants of the cultivar Managua Orange in the following characteristics:

1. Plants of the new *Chrysanthemum* had thinner stems than plants of the cultivar Managua Orange.
2. Plants of the new *Chrysanthemum* had smaller leaves than plants of the cultivar Managua Orange.
3. Plants of the new *Chrysanthemum* had larger inflorescences than plants of the cultivar Managua Orange.
4. Ray florets of plants of the new *Chrysanthemum* were flatter and straighter than ray florets of plants of the cultivar Managua Orange.

Plants of the new *Chrysanthemum* can also be compared to plants of the *Chrysanthemum* cultivar Tiger, disclosed in U.S. Plant Pat. No. 14,051. In side-by-side comparisons conducted in Hensbroek, The Netherlands, plants of the new *Chrysanthemum* differed primarily from plants of the cultivar Tiger in the following characteristics:

1. Plants of the new *Chrysanthemum* had narrower stems than plants of the cultivar Tiger.
2. Plants of the new *Chrysanthemum* had narrower ray florets than plants of the cultivar Tiger.

3. Plants of the new *Chrysanthemum* flowered earlier than plants of the cultivar Tiger.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'DekLacetti'.

The photograph at the bottom left of the sheet comprises a close-up view of upper surface of a typical inflorescence and a typical leaf of 'DekLacetti'.

The photograph at the bottom right of the sheet comprises a close-up view of lower surface of a typical inflorescence and a typical leaf of 'DekLacetti'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the winter in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5 to 22° C., night temperatures were about 18.5° C. and light levels were about five kilolux. Plants were pinched once and were about twelve weeks from planting when the photographs and the description were taken.

Botanical classification: *Chrysanthemum×morifolium* cultivar DekLacetti.

Commercial classification: Daisy type *Chrysanthemum* typically grown as a spray-type cut flower.

Parentage:

*Female or seed parent.*—Proprietary selection of *Chrysanthemum×morifolium* identified as code number 5003,75, not patented.

*Male or pollen parent.*—Proprietary selection of *Chrysanthemum×morifolium* identified as code number 99.619,01, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous daisy type cut *Chrysanthemum*; typically grown as a spray type; erect and strong flowering stems.

*Growth rate.*—Moderate; moderately vigorous.

*Flowering stem description.*—Length: About 90 cm. Diameter: About 5 mm. Strength: Strong. Aspect: Erect. Branching habit: Plants are typically grown as single stems. Color: 146B.

*Foliage description.*—Arrangement: Alternate. Length: About 9 to 10.5 cm. Width: About 7 to 8.5 cm. Apex: Cuspidate. Base: Truncate. Margin: Pinnately lobed; serrate. Texture, upper and lower surface: Pubescent. Petiole length: About 2 cm. Color: Developing foliage, upper surface: 137A. Developing foliage, lower surface: 146B. Fully expanded foliage, upper surface: 137A. Fully expanded foliage, lower surface: Between 146A and 147B. Venation, upper surface: 147B. Venation, lower surface: 146B. Petiole: 146B.

Inflorescence description:

*Appearance.*—Daisy type inflorescence form with elongated oblong to roughly spatulate-shaped ray florets. Inflorescences borne on terminals above foliage. Disk and ray florets develop acropetally on a capitulum. Not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 53 days later. Early and uniform flowering response.

*Postproduction longevity.*—Cut inflorescences will maintain good substance and form for about 3.5 weeks.

*Quantity of inflorescences per flowering stem.*—About 20 inflorescences per flowering stem.

*Inflorescence size.*—Diameter: About 7 cm. Depth (height): About 3 cm. Diameter of disc: About 1.75 cm.

*Inflorescence buds.*—Length: About 1 cm. Diameter: About 1.1 cm. Shape: Oblate. Color: 137C.

*Ray florets.*—Length: About 3 to 3.2 cm. Width: About 1 cm. Shape: Elongated oblong to roughly spatulate. Apex: Rounded. Base: Fused, short corolla tube. Margin: Entire. Texture, upper and lower surfaces: Smooth, glabrous. Number of ray florets per inflorescence: About 25. Color: When opening, upper and lower surfaces: 163B. Fully opened, upper surface: 163B. Fully opened, lower surface: 163C.

*Disc florets.*—Shape: Tubular. Length: About 4 mm. Width: About 1 mm. Number of disc florets per inflorescence: About 200 to 230. Color: Immature: Towards the apex, 144A; towards the base, 145C overlain with 153D. Mature: 153D.

*Peduncles.*—Length, terminal peduncle: About 2 cm. Length, fourth peduncle: About 7.5 cm. Diameter: About 3 mm. Strength: Moderately strong to strong. Texture: Pubescent. Color: 146B.

*Reproductive organs.*—Androecium: Present on disc florets only. Gynoecium: Present on both ray and disc florets.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'DekLacetti', as illustrated and described.

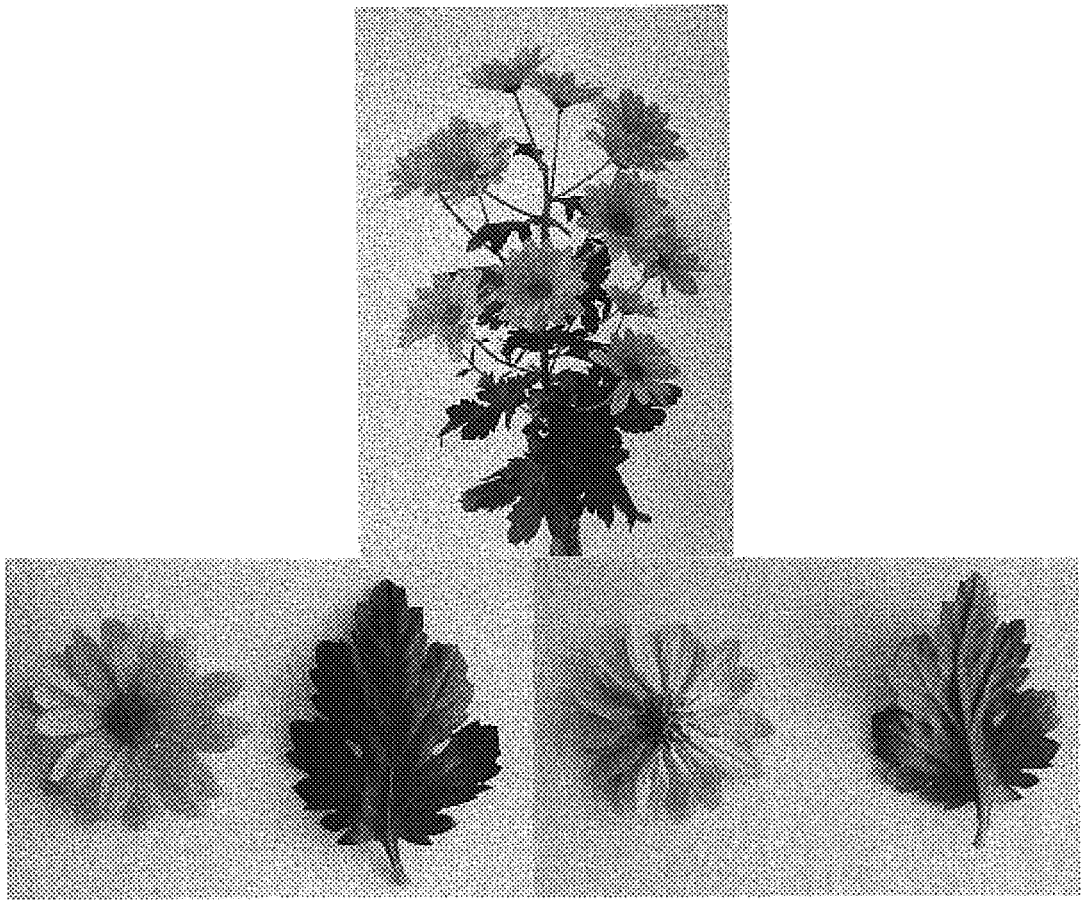

* * * * *